(12) United States Patent
Patwardhan

(10) Patent No.: US 9,901,375 B2
(45) Date of Patent: *Feb. 27, 2018

(54) SURGICAL NAVIGATION

(71) Applicant: Interactive Neuroscience Center, LLC, Shreveport, LA (US)

(72) Inventor: Ravish Patwardhan, New York, NY (US)

(73) Assignee: Interactive Neuroscience Center, LLC, Shreveport, LA (US)

( * ) Notice: Subject to any disclaimer, the term of this patent is extended or adjusted under 35 U.S.C. 154(b) by 6 days.

This patent is subject to a terminal disclaimer.

(21) Appl. No.: 14/949,094

(22) Filed: Nov. 23, 2015

(65) Prior Publication Data

US 2016/0074068 A1 Mar. 17, 2016

Related U.S. Application Data

(63) Continuation of application No. 13/773,181, filed on Feb. 21, 2013, now Pat. No. 9,192,400, which is a
(Continued)

(51) Int. Cl.
*A61B 17/16* (2006.01)
*A61B 17/17* (2006.01)
(Continued)

(52) U.S. Cl.
CPC ...... *A61B 17/3472* (2013.01); *A61B 17/1662* (2013.01); *A61B 17/1695* (2013.01);
(Continued)

(58) Field of Classification Search
CPC . A61B 17/1695; A61B 17/1739; A61B 90/10; A61B 90/11
See application file for complete search history.

(56) References Cited

U.S. PATENT DOCUMENTS 3,021,842 A * 2/1962 Flood .................. A61B 90/11
604/175
4,186,728 A 2/1980 van Lotringen
(Continued)

FOREIGN PATENT DOCUMENTS

EP 2124799 A1 12/2009
FR 2124799 A5 9/1972
(Continued)

OTHER PUBLICATIONS

Benardete et al., "Comparison of frameless stereotactic systems: accuracy, precision, and applications," Neurosurgery. Dec. 2001, 49(6), pp. 1409-1415, discussion 1415-1416.
(Continued)

*Primary Examiner* — Nicholas Woodall
(74) *Attorney, Agent, or Firm* — Harness Dickey

(57) ABSTRACT

A method of surgical navigation into the brain includes establishing a trajectory through the skull into the brain to a target, drilling a hole in the skull using a drill, and verifying the trajectory of the drilled hole during drilling using image guidance. A surgical navigation system includes a cannulated drill, a cannulated access member, and a coupling member for coupling the access member to the drill and for maintaining alignment of the cannulations in the drill and the access member. The access member is movable relative to the coupling member such that the access member can be secured to tissue while the coupling member maintains the alignment of the cannulations. A surgical kit includes a cannulated drill, a cannulated access member, a coupling member for coupling the access member to the drill, and a probe for receipt within the cannulated drill.

20 Claims, 5 Drawing Sheets

Related U.S. Application Data continuation of application No. 12/525,492, filed as application No. PCT/US2008/052790 on Feb. 1, 2008, now Pat. No. 8,394,099.

(60) Provisional application No. 60/942,261, filed on Jun. 6, 2007, provisional application No. 60/887,719, filed on Feb. 1, 2007.

(51) Int. Cl.
| | |
|---|---|
| *A61B 90/10* | (2016.01) |
| *A61B 90/11* | (2016.01) |
| *A61B 17/34* | (2006.01) |
| *A61B 90/00* | (2016.01) |
| *A61B 34/20* | (2016.01) |
| *A61B 90/14* | (2016.01) |
| *A61B 34/10* | (2016.01) |

(52) U.S. Cl.
CPC .......... *A61B 17/17* (2013.01); *A61B 17/1703* (2013.01); *A61B 17/1739* (2013.01); *A61B 90/36* (2016.02); *A61B 17/1637* (2013.01); *A61B 34/20* (2016.02); *A61B 90/11* (2016.02); *A61B 90/14* (2016.02); *A61B 2017/349* (2013.01); *A61B 2034/107* (2016.02); *A61B 2090/103* (2016.02)

(56) References Cited

U.S. PATENT DOCUMENTS

| | | | |
|---|---|---|---|
| 4,362,161 A | | 12/1982 | Reimels et al. |
| 4,681,103 A | * | 7/1987 | Boner .................. A61B 5/6864 600/461 |
| 4,821,716 A | * | 4/1989 | Ghajar ............... A61B 17/1695 604/174 |
| 4,903,707 A | | 2/1990 | Knute et al. |
| 4,979,949 A | | 12/1990 | Matsen, III et al. |
| 5,116,345 A | | 5/1992 | Jewell et al. |
| 5,800,557 A | | 9/1998 | Elhami et al. |
| 6,432,058 B1 | | 8/2002 | Sloth |
| 7,780,679 B2 | | 8/2010 | Bobo, Sr. et al. |
| 8,394,099 B2 | | 3/2013 | Patwardhan |
| 9,192,400 B2 | | 11/2015 | Patwardhan |
| 2002/0193800 A1 | | 12/2002 | Kienzle et al. |
| 2005/0020909 A1 | | 1/2005 | Moctezuma de la Barrera et al. |
| 2005/0065515 A1 | | 3/2005 | Jahng |
| 2005/0251144 A1 | | 11/2005 | Wilson et al. |
| 2006/0084867 A1 | | 4/2006 | Tremblay et al. |
| 2006/0149280 A1 | | 7/2006 | Harvie et al. |
| 2013/0165937 A1 | | 6/2013 | Patwardhan |

FOREIGN PATENT DOCUMENTS

| | | |
|---|---|---|
| GB | 2124799 A | 2/1984 |
| TW | I461176 B | 11/2014 |
| WO | WO-2006078677 A2 | 7/2006 |
| WO | WO-2008095166 A1 | 8/2008 |

OTHER PUBLICATIONS

Bernays et al., "A new artifact-free device for frameless, magnetic resonance imaging-guided stereotactic procedures," Neurosurgery. Jan. 2000, 46(1), pp. 112-116; discussion 116-117.

Dorward et al., "Accuracy of true frameless stereotaxy: in vivo measurement and laboratory phantom studies. Technical note," J Neurosurg., Jan. 1999, 90(1), pp. 160-168.

Dorward et al., "The advantages of frameless stereotactic biopsy over frame-based biopsy," Br J Neurosurg., Apr. 2002, 16(2), pp. 110-118. Comment in: Br J Neurosurg., Feb. 2003, 17(1), pp. 90-91, Author Reply 91.

Examination Search Report dated Jul. 16, 2015 for Canadian Patent Application No. 2,677,239 claiming benefit of PCT/US2008/052790.

EPO Communication Pursuant to Article 94(3) EPC, dated Sep. 15, 2010, 5 pages.

Gil et al., "Ventricular catheter placement in children with hydrocephalus and small ventricles: the use of a frameless neuronavigation system," Childs Nerv Syst., Feb. 2002, 18(1-2), pp. 26-29, Epub Jan. 26, 2002.

Golfinos et al., "Clinical use of a frameless stereotactic arm: results of 325 cases," J Neurosurg., Aug. 1995, 83(2), pp. 197-205.

Heilbrun et al., "Preliminary expereience using an optimized three-point transformation algorithm for spatial registration of coordinate systems: a method of noninvasive localization using frame-based stereotactic guidance systems," J Neurosurgy, Nov. 1994, 81(5), pp. 676-682.

Henderson, "Frameless localization for functional neurosurgical procedures: a preliminary accuracy study," Stereotact Funct Neurosurg. 2004, 82(4), pp. 135-141, Epub Oct. 4, 2004.

Holloway et al., "Frameless stereotaxy using bone fiducial markers for deep brain stimulation," J Neurosurg., Sep. 2005, 103(3), pp. 404-413.

Holly et al., "Percutaneous placement of posterior cervical screw using three-dimensional fluroscopy," Spine, Mar. 1, 2006, 31(5), pp. 536-540, discussion 541.

Housepian, "Stereotactic surgery: the early years," Neurosurgery, Nov. 2004; 55(5), pp. 1210-1214.

International Search Report, PCT/US2008/052790, dated Jul. 2, 2008, 3 pages.

Jung et al., "Application of neuronavigation system to brain tumor surgery with clinical experience of 420 cases," Minim Invasive Neurosurg., Aug. 2006, 49(4), pp. 210-215.

Kamimura et al., "Cervical pedicle screw insertion: assessment of safety and accuracy with computer-assisted image guidance," J Spinal Disord. Jun. 2000; 13(3), pp. 218-224. Comment in: J Spinal Disord, Aug. 2000, 13(4), p. 275.

Kim et al., "Universal calibration of surgical instruments for spinal stereotaxy," Neurosurgery, Jan. 1999, 44(1), pp. 173-177, discussion 177-178.

Lunsford et al., "stereotactic implantation of deep brain electrodes using computed tomography," Neurosurgery, Sep. 1983; 13(3), pp. 280-286.

Mascott, C.R., "In vivo accuracy of image guidance performed using optical tracking and optimized registration," J Neurosurg., Oct. 2006, 105(4), p. 561-567.

Mehta et al.,; "Frameless stereotactic placement of depth electrodes in epilepsy surgery," J Neurosurg. Jun. 2005, 102(6), pp. 1040-1045.

Moriarty et al., "Frameless stereotactic neurosurgery using intraoperative magnetic resonance imaging: stereotactic brain biopsy," Neurosurgery, Nov. 2000, 47(5), pp. 1138-1145, discussion 1145-1146.

Muacevic et al., "Accuracy and clinical applicability of a passive marker based frameless neuronavigation syste," J Clin Neurosci., Sep. 2000, 7(5), pp. 414-418.

Murphy et al., "Insertion of depth electrodes with or without subdural grids using frameless stereotactic guidance systems— technique and outcome," Br J Neurosurg., Apr. 2002; 16(2), pp. 119-125.

Murphy, "An automatic six-degree-of-freedom image registration algorithm for image-guided fameless stereotaxic radiosurgery," Med Phys., Jun. 1997, 24(6), pp. 857-866.

PCT International Preliminary Report on Patentability and Written Opinion of the International Searching Authority, PCT/US2008/052790, dated Aug. 13, 2009, 9 pages.

Quinones-Hinojosa et al., "Assessment of image guided accuracy in a skull model: comparison of frameless stereotaxy techniques frame-based localization," J Neurooncol., Jan. 2006, 76(1), pp. 65-70.

Rachinger, J. et al., "Application accuracy of automatic registration in frameless stereotaxy," Stereotact Funct Neurosurg, 2006, 84(2-3), pp. 109-117, Epub Jul. 10, 2006.

(56) References Cited

OTHER PUBLICATIONS

Reinges et al., "Experience with a new multifunctional articulated instrument holder in minimally invasive navigated neurosurgery," Minim Invasive Neurosurgy, Sep. 1998, 41(3), pp. 149-151.

Smith et al., "Frame-based stereotactic biopsy remains an important diagnostic tool with distinct advantages over frameless steroatactic biopsy," J Neurooncol. Jun. 2005; 73(2), pp. 173-179.

Spivak et al., "Comparison fo the reliability of brain lesion localization when using traditional and stereotactic image-guided techniques: a prosepctive study," J Neurosurg., Sep. 2005, 103(3), pp. 424-427.

Tirakotai et al., "Clinical application of neuro-navigation in a series of single burr-hole procedures," Zentralbl Neurochir., May 2004, 65(2), pp. 57-64.

Van Roost et al., "Depth electrode implantation in the length axis of the hippocampus for the presurgical evaluation of medial temporal lobe epilepsy: a computed tomography-based stereotactic insertion technique and its accuracy," Neurosurgery, Oct. 1998, 43(4), pp. 819-826, discussion 826-827.

Woerdeman et al., "Frameless stereotactic placement of ventriculoperitoneal shunts in undersized ventricles: a simple modification to free-hand procedures," Br J. Neurosurg., Dec. 2005, 19(6), pp. 484-487.

Woodworth et al., "Frameless image-guided stereotactic brain biopsy procedure: diagnostic yield, surgical morbidity, and comparison with the frame-based technique," J Neurosurg., Feb. 2006, 104(2), pp. 233-237.

Catalogue listing for Stryker 2102 Complete Set Orthopedic, 1 pages.

Dorward et al., "Clinical introduction of an adjustable rigid instrument holder for frameless stereotactic interventions," Comput Aided Surg., 1997, 2(3-4), pp. 180-185.

Doshi et al., "Frameless stereotaxy and interactive neurosurgery with thhe ISG viewing wand," Acta Neurochir Suppl., 1995, 64, pp. 49-53.

Eljamel, "Accuracy, efficacy, and clinical application sof the Radionics Operating Arm System," Comput Aided Surg., 1997, 2(5), pp. 292-297.

Eljamel, "Frameless stereotactic neurosurgery: two steps towards the Holy Grail of surgical navigation," Stereotact Funct Neurosurg., 1999, 72(2-4), pp. 125-128.

Germano et al., "Clincial expereience with intracranial brain needle biopsy using frameless surgical navigation," Comput Aided Surg., 1998, 3(1), pp. 33-39.

Gralla et al., "Frameless stereotactic brain biopsy procedures using the stealth Station: indications, accuracy and results," Zentralbl Neurochir, 2003, 64(4), pp. 166-170.

Helm et al., "Accuracy of registration methods in frameless stereotaxis," Comput Aided Surg., 1998, 3(2), pp. 51-56.

Kim et al., "New software applications for interchangeable instrumentation in spinal stereotaxis," Stud Health Technol Inform, 1999, 62, pp. 179-180.

Kratimenos et al., "multimodal imaging integration and stereotactic intracerebral electrode insertion in the investigation of drug resistant epilepsy," Acta Neurochir Suppl (Wien), 1993, 58, pp. 186-189.

Kratimenos et al., "Stereotactic insertion of intracerebral electrodes in the investigation of epilepsy," Br J Neurosurgy, 1993, 7(1), pp. 45-52.

Kremser et al., "Image registration of MR and CT images using a frameless fiducial marker system," Magn Reson Imaging, 1997, 15(5), pp. 579-585.

Leung et al., "Practice of Intramedullary Locked Nails: New Developments in Techniques and Applications," Springer-Verlag, 2006, pp. 243-263.

Patel et al., "A simple trajectory guidance device that assists freehand and interactive image guided biopsy of small deep intracranial targets," Comput Aided Surg., 1997, 2(3-4), pp. 186-192.

Steinmeier et al., "Factors influencing the application accuracy of neuronavigation systems," Stereotact Funct Neurosurg. 2000, 75(4), pp. 188-202.

Tronnier et al., "Intraoperative computer-assisted neuronavigation in functional neurosurgery," Stereotact Funct Neurosurg., 1996, 66(1-3), pp. 65-68.

Vinas et al., "Application accuracy study of a semipermanent fiducial system for frameless stereotaxis," Comput Aided Surg: 1997, 2(5), pp. 257-263.

Canadian Office Action dated Jun. 19, 2017 in corresponding Canadian Application No. 2,920,553.

Thai Office Action dated Aug. 25, 2017 in corresponding Thai Application No. 0801000530.

Canadian Office Action dated Oct. 31, 2017 in corresponding Canadian Application No. 2,920,567.

* cited by examiner

SURGICAL NAVIGATION

CROSS-REFERENCE TO RELATED APPLICATIONS

This application is a continuation of U.S. patent application Ser. No. 13/773,181 filed on Feb. 21, 2013, which is a continuation of U.S. patent application Ser. No. 12/525,492 filed on Jan. 6, 2010, now U.S. Pat. No. 8,394,099 issued on Mar. 12, 2013, which claims benefit of International Patent Application No. PCT/US2008/052790 filed on Feb. 1, 2008, which claims benefit of: (1.) U.S. Patent Application No. 60/942,261 filed on Jun. 6, 2007, and (2.) U.S. Patent Application No. 60/887,719 filed on Feb. 1, 2007. The entire disclosures of each of the above applications are incorporated herein by reference.

FIELD

The present disclosure relates to surgical navigation.

SUMMARY

This section provides a general summary of the disclosure, and is not a comprehensive disclosure of its full scope or all of its features.

A method of surgical navigation into the brain includes establishing a trajectory through the skull into the brain to a target, drilling a hole in the skull using a drill, and verifying the trajectory of the drilled hole during drilling using image guidance.

Embodiments of this aspect may include one or more of the following features. The image guidance is provided by a probe received by the drill. The probe is received in a lumen defined by the drill. The method includes placing an access member in the drilled hole, and verifying the trajectory of the access member during placement. The access member is placed using the drill, and the trajectory is verified using the probe received by the drill.

A surgical navigation system includes a cannulated drill, a cannulated access member, and a coupling member for coupling the access member to the drill and for maintaining alignment of the cannulations in the drill and the access member. The access member is movable relative to the coupling member such that the access member can be secured to tissue while the coupling member maintains the alignment of the cannulations.

Embodiments of this aspect may include one or more of the following features. The system includes a probe for receipt within the cannulated A surgical kit includes a cannulated drill, a cannulated access member, a coupling member for coupling the access member to the drill, and a probe for receipt within the cannulated drill. Embodiments of this aspect may also include a drill bit, a medical device, and/or a robot arm.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
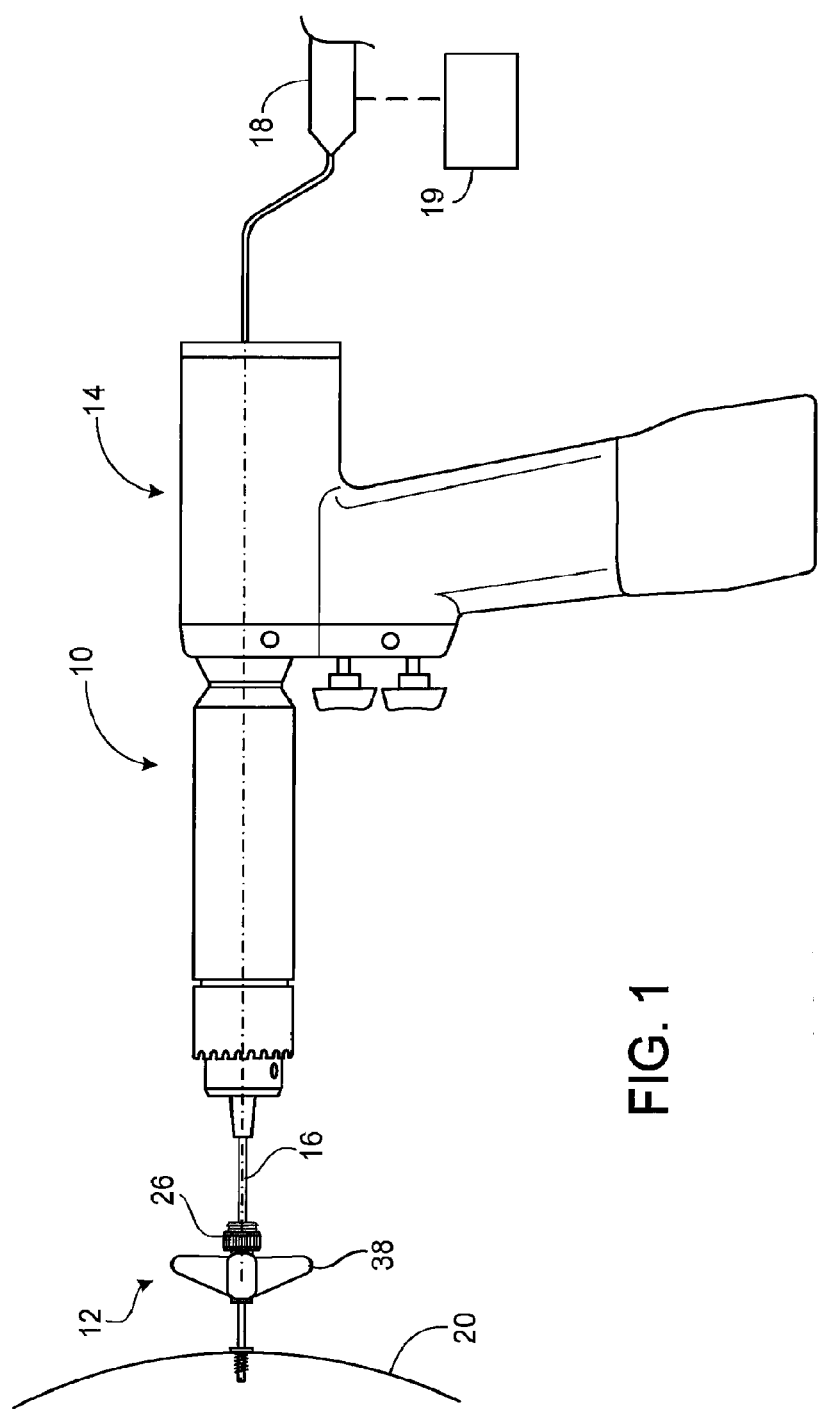
FIG. 1 is an illustration of a cannulated drill being used to place an access member in the skull under navigation guidance.

Referring to FIG. 1, an image-guided trajectory system 10 includes an access member 12 for establishing a set trajectory to a target site, a cannulated drill 14, and a coupling member rod 16 that couples the access member 12 to the cannulated drill 14 during securement of the access member 12 to a patient's skull 20. Also shown in FIG. 1 is a probe 18, for example, a BrainLab Probe (available from BrainLab Cranial Navigation System) or an Integra Probe (available from Integra LifeSciences), received within the drill 14 and extending about half-way down the length of the drill 14. The probe 18 is coupled to an image guidance system 19, for example, a BrainLab image guidance system or an Integra image guidance system, which tracks the trajectory of the probe 18 relative to images of a patient's brain. The receipt of the probe 18 within the cannulated drill 14 during securement of the access member 12 to the skull 20 insures that the access member 12 establishes the desired trajectory to a target site.

Figure 2:
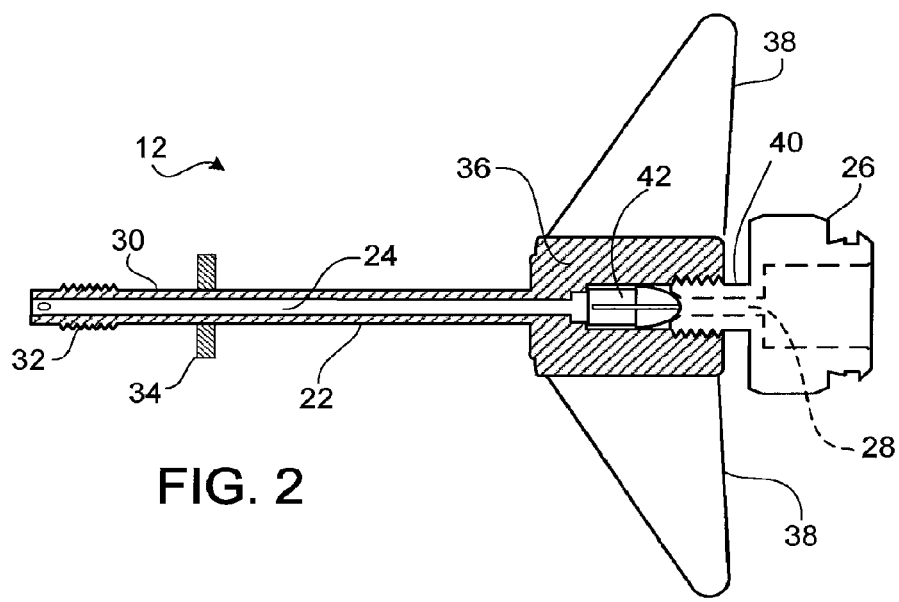
FIG. 2 is a partial cross-sectional view of the access member.

Referring to FIG. 2, the access member 12 includes a main body 22 defining an internal lumen 24, and a clamping member 26 defining an internal lumen 28 aligned with lumen 24. The main body 22 has a distal portion 30 with a threaded region 32 that engages the skull bone to secure the access member to the skull 20. Surrounding the distal portion 30 is a depth stop 34 that sets the depth to which the access member 12 is insertable into the skull. The main body 22 has a proximal portion 36 with two outwardly extending wings 38 that can be engaged by the operator's hand and turned to thread the access member 12 into the skull.

Figure 3:
FIG. 3 is a side view of a coupling member that couples the access member to the cannulated drill.

The clamping member 26 has a threaded extension 40 that is received by the proximal portion 36 of the main body 24 and is rotatable relative to the main body 24. The clamping member 26 acts on a collet 42 located within proximal portion 36 such that rotation of the clamping member 26 causes the collet 42 to clamp onto and release the rod 16 (FIG. 3) received in the lumens 24 and 28.

Figure 4:
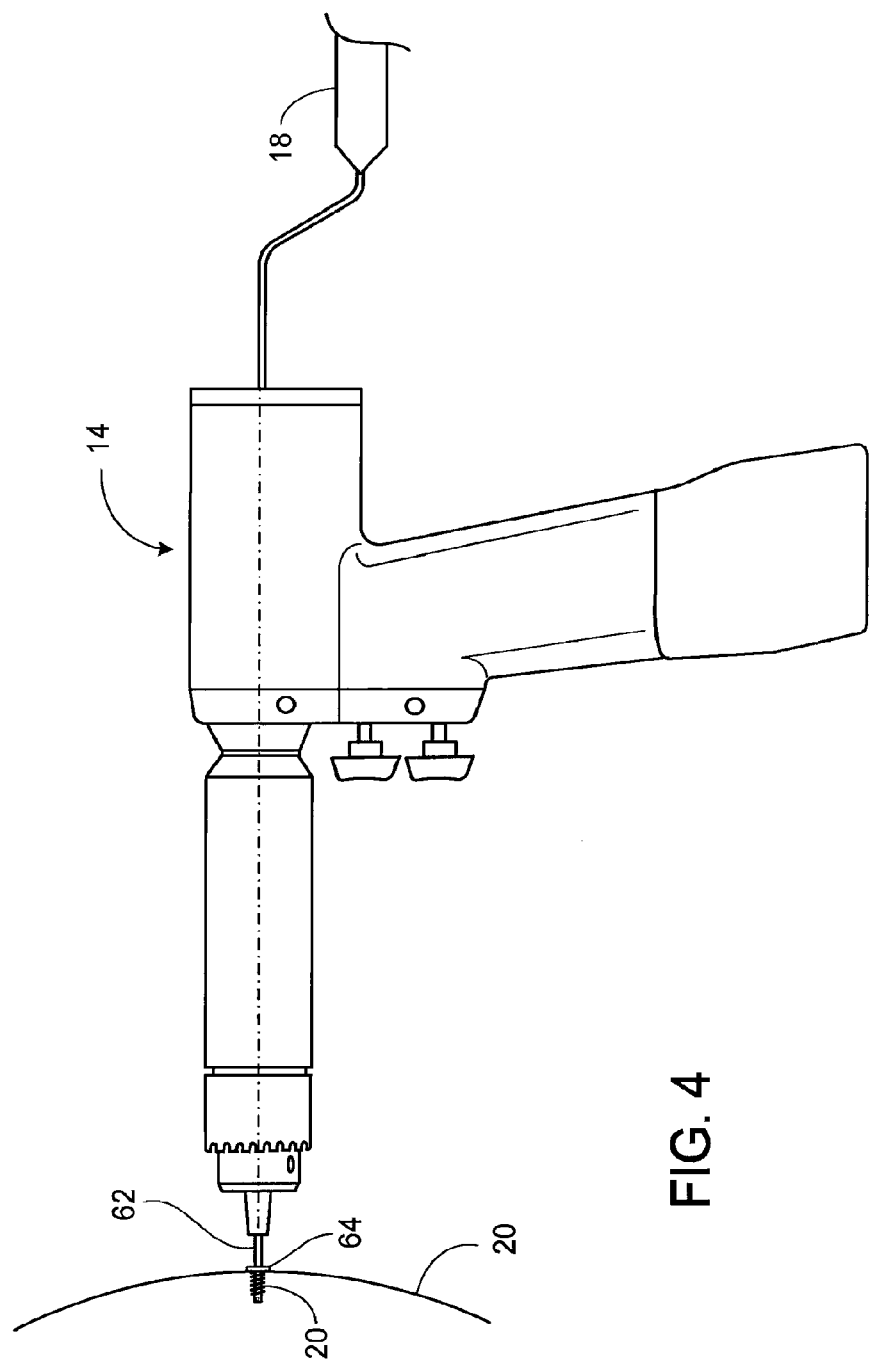
FIG. 4 shows the cannulated drill being used to drill a hole in a skull.

Referring to FIG. 4, prior to securing the access member 12 to the skull 20, the operator uses the cannulated drill 14 to drill a pilot hole 60 in the skull 20. Using a drill bit 62 and with the probe 18 received within the drill 14, the operator drills the pilot hole 60 under image guidance such that the pilot hole 60 is aligned with a desired preplanned trajectory to a target set within the brain. Surrounding the drill bit 62 is a movable depth stop 64 that sets the depth to which the drill bit 62 is insertable into the skull.

After drilling the pilot hole, the operator replaces the drill bit 62 with the rod 16 and attached access member 12, a shown in FIG. 1. The rod 16 extends about 3.5 cm into the drill 14 and about 3.5 cm into the access member 12 to axially align the drill 14 and the access member 12. The operator places the access member 12 against the entrance to the pilot hole 60 and uses the probe 18 to align the access member 12 along the desired trajectory to the target site. The operator then loosens the collet 26 such that the access member 12 can be rotated relative to the rod 16 to advance the access member 12 into the skull 20. While the rod remains attached to the drill 14 and remains within the lumens 24, 28 during rotation of the access member 12, the rod 16 need not move, that is, is not rotated, during the advancement of the access member 12. While applying a force to the wings 38 to thread the access member 12 into the skull 20, the operator verifies the alignment of the access member 12 along the trajectory using probe 18 positioned within drill 14.

Figure 5:
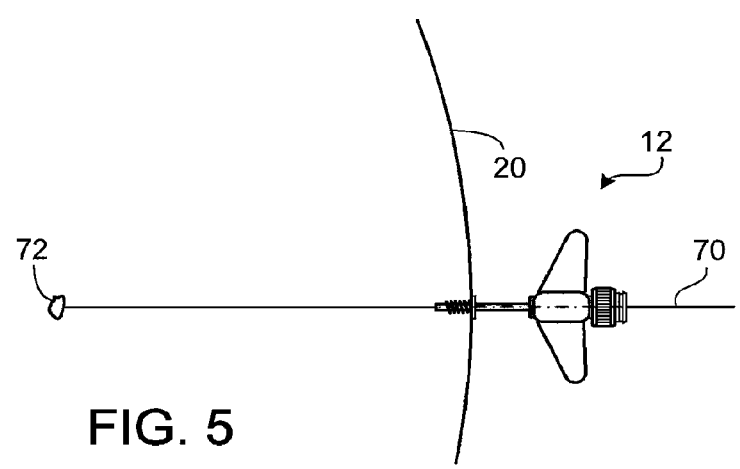
FIG. 5 shows the access member being used to position a medical device at a target site within the brain.

The operator then removes the drill 14 and rod 16 from the access member 12. Referring to FIG. 5, the access member 12 now establishes a set trajectory for introduction of various medical devices 70, e.g., ventriculostomy catheters, other directed catheters for convection therapy, epilepsy depth electrodes, thermocoagulation probes, lesioning probes, stereotactic needles, and ablative probes, to the target site 72. The operator need only control the depth of advancement of the medical device, which, in many cases, can be predetermined using navigation software.

To further increase the accuracy of the device placement through the access member 12, the drill 14 can directly hold the access member after securement of the access member to the skull 20, and the medical device can be passed through the drill and the access member to the target site.

A cannulated drill is available from Stryker (4200 Cordless Driver 2), and can be used with a step down chuck for holding the drill bit 62 and the rod 16.

Figure 6:
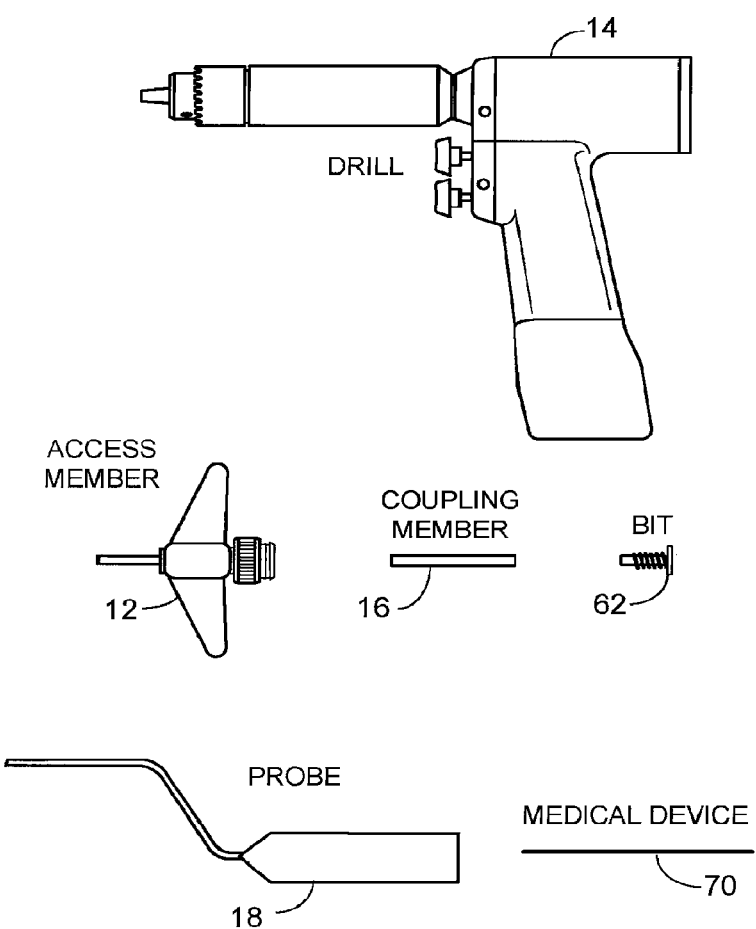
FIG. 6 illustrates an exemplary disposable kit containing components of the system.

The various components of the image-guided trajectory system 10 can be sold as kits 80 (FIG. 6), either disposable or non disposable, including one or more components of the system 10. For example, the cannulated drill 14, the access member 12, the coupling member 16, and the drill bit 62 can be packaged together for sale as a disposable kit. Alternatively, any combination of one or more of the foregoing components can be packaged together for sale as a disposable kit, for example, just the access member 12, the coupling member 16, and the drill bit 62 can be packaged together, the access member 12 and the coupling member 16 can be packaged together, etc. The probe 18 can also be included in any of the various combinations of disposable kits described above, for example, a disposable kit can include the probe 18, drill 14, access member 12, and coupling member 16. Furthermore, one or more medical devices 70 can be included in any of the various combinations of disposable kits, including kits with the probe 18. All of the components need not be disposable. The various components can be sold as a system with the image guidance system 19.

Figure 7:
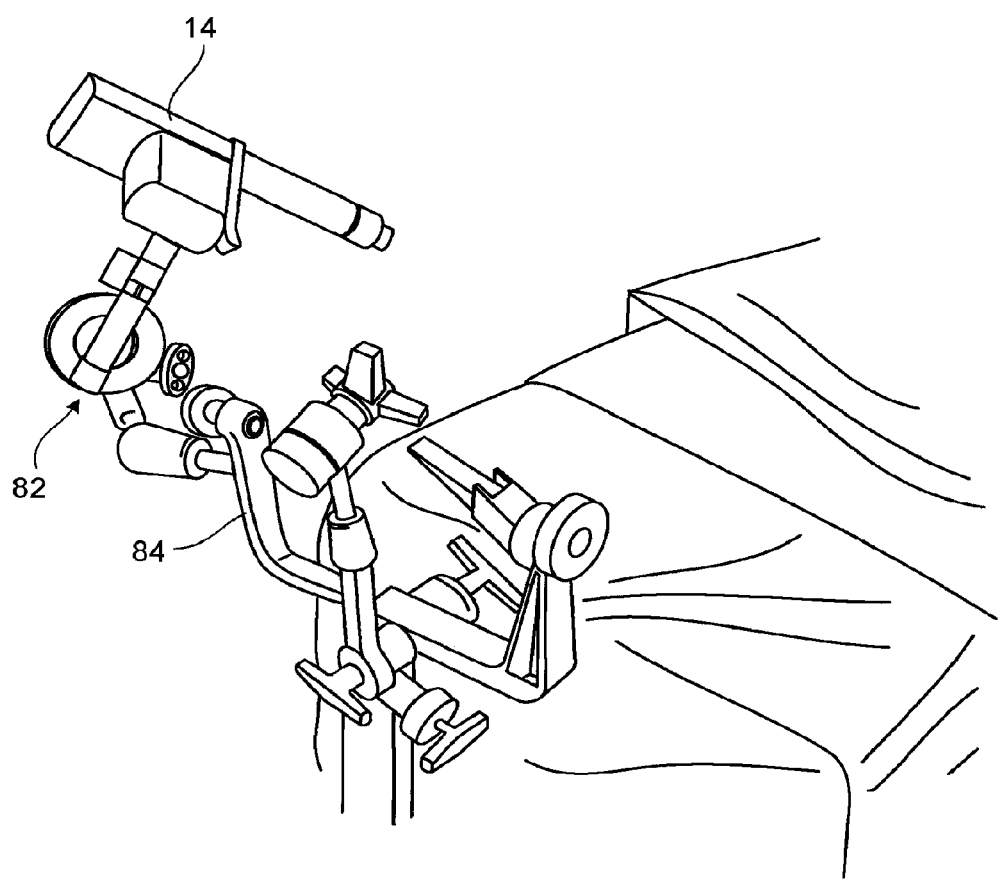
FIG. 7 illustrates a robot arm supporting the cannulated drill.

Referring to FIG. 7, the cannulated drill 14 can be supported during use by a robot arm 82, for example, a BrainLab robot arm. The robot arm 82 can be manipulated to fix the position of the cannulated drill 14 in a selected axis. The robot arm 82 is preferably supported by a device 84, for example, a Mayfield head holder, used to fixate the head. The robot arm 82 can be included in any of the kit configurations described above.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system comprising:
   a coupling rod; and
   an access member having,
   a main body defining a first lumen extending from a proximal end to a distal end of the main body, the proximal end having a first coupling region and the distal end having a second coupling region;
   a clamping member coupled to the first coupling region and defining a second lumen aligned with the first lumen; and
   a collet at the proximal end of the main body configured to secure the coupling rod received in the first and second lumens, the collet (i) is caused to clamp down on the coupling rod by the clamping member when the access member is tightened onto the clamping member, and (ii) releases the coupling rod when the access member is loosened from the clamping member;
   wherein the second coupling region is configured to be coupled to a bone of a patient and the proximal end is configured to receive a medical device through the second lumen of the clamping member and the first lumen of the main body;
   wherein the access member, while coupled to the clamping member, is movable relative to the clamping member to secure the access member to the bone of a patient while the clamping member and the coupling rod maintain alignment of the first lumen and the second lumen.

2. The system of claim 1, wherein the access member further includes a depth stop positioned on the main body and configured for setting a depth to which the access member is insertable into the bone of the patient.

3. The system of claim 1, wherein the second coupling region is an external threaded region configured to be threadably received within the bone of the patient.

4. The system of claim 1, wherein the proximal end of the main body includes two outwardly extending wings for facilitating advancing of the access member into the bone of the patient.

5. The system of claim 1, wherein the clamping member has an externally threaded extension and is threadably coupled to an internal thread of the first coupling region of the main body, wherein the clamping member is rotatable relative to the main body.

6. The system of claim 1, further comprising a cannulated drill configured to receive the coupling rod to maintain an alignment of a cannulation in the cannulated drill and the first and second lumens.

7. The system of claim 6, further comprising a probe configured to be disposed within the cannulated drill and configured to guide alignment of the access member to a target in the patient.

8. The system of claim 6, further comprising a robot arm configured to fix a position of the cannulated drill in a selected axis.

9. The system of claim 6, further comprising a drill bit configured to be attached to the cannulated drill and configured for drilling a pilot hole into the bone.

10. The system of claim 1, further comprising the medical device.

11. The system of claim 10, wherein the medical device comprises a ventriculostomy catheter, convertion therapy catheter, epilepsy depth electrode, thermocoagulation probe, lesioning probe, stereotactic needle or ablative probe.

12. A system comprising:
a cannulated drill;
a coupling rod; and
an access member having,
a body extending from a proximal end to a distal end and defining a first lumen extending therethrough;
a first coupling mechanism at the proximal end configured to receive and secure the coupling rod received in the first lumen; and
a second coupling at the distal end configured to be coupled to a bone of a patient and defining a second lumen aligned with the first lumen;
wherein the first lumen and the second lumen are is configured to receive and guide a medical device to the patient,
wherein the coupling rod is received within the cannulated drill, the first lumen, and the second lumen;
wherein the first coupling mechanism couples the access member to the cannulated drill with the coupling rod;
wherein the access member, while coupled to the first coupling mechanism, is movable relative to the first coupling mechanism to secure the access member to the bone of the patient while the first coupling mechanism and the coupling rod maintain alignment of the first lumen and the second lumen.

13. The system of claim 12, wherein a first coupling mechanism includes a clamping member coupled to the proximal end.

14. The system of claim 13, further comprising a collet at the proximal end of the body configured to secure the coupling rod received in the first and second lumens, the collet (i) is caused to clamp down on the coupling rod by the clamping member when the access member is tightened onto the clamping member, and (ii) releases the coupling rod when the access member is loosened from the clamping member.

15. The system of claim 12, wherein the second coupling includes an external threaded region configured to be threadably received within the bone of the patient.

16. The system of claim 15, wherein the access member further includes a depth stop positioned on the body adjacent to the external threaded region configured for setting a depth to which the access member is threadably inserted into the bone of the patient.

17. The system of claim 16, wherein the proximal end of the body includes two outwardly extending wings configured to facilitate advancing the access member into the bone of the patient.

18. The system of claim 12, further comprising:
the cannulated drill configured to receive the coupling rod to maintain an alignment of a cannulation in the cannulated drill and the first and second lumens.

19. A system comprising:
a coupling rod; and
an access member having,
a main body extending from a proximal end to a distal end and defining a first lumen extending therethrough;
a bone engaging coupling at the distal end of the main body configured to be coupled to a bone of a patient;
a depth stop positioned on the main body adjacent to the bone engaging coupling configured to set a depth to which the access member is insertable into the bone of the patient;
a clamping member extending from the proximal end and defining a second lumen aligned with the first lumen; and
a collet at the proximal end of the main body configured to secure the coupling rod received in the first and second lumens, the collet (i) is caused to clamp down on the coupling rod by the clamping member when the access member is tightened onto the clamping member, and (ii) releases the coupling rod when the access member is loosened from the clamping member;
wherein upon the coupling rod being received in the first and second lumens, the clamping member is configured to rotate and secure the coupling rod in the first and second lumens with the collet;
wherein the access member, while coupled to the clamping member, is movable relative to the clamping member to secure the access member to the bone of a patient while the clamping member and the coupling rod maintain alignment of the first lumen and the second lumen.

20. The system of claim 19 further comprising:
a cannulated drill configured to receive the coupling rod; and
a trackable probe configured to be received by the cannulated drill;
wherein a cannulation of the cannulated drill is tracked by way of the trackable probe to maintain an alignment of the cannulation in the cannulated drill with the first and second lumens using the coupling rod and aligning a trajectory of a medical device with the trackable probe.

* * * * *

UNITED STATES PATENT AND TRADEMARK OFFICE
CERTIFICATE OF CORRECTION

PATENT NO. : 9,901,375 B2
APPLICATION NO. : 14/949094
DATED : February 27, 2018
INVENTOR(S) : Ravish Patwardhan It is certified that error appears in the above-identified patent and that said Letters Patent is hereby corrected as shown below:

On the Title Page

Page 2, Column 2, Line 12, Other Publications: Delete "expereience" and insert --experience-- therefore;

Page 2, Column 2, Line 24, Other Publications: Delete "fluroscopy," and insert --fluoroscopy,-- therefore;

Page 2, Column 2, Line 46, Other Publications: Delete "Mehta et al.,," and insert --Mehta et al.,-- therefore;

Page 2, Column 2, Line 53, Other Publications: Delete "syste," and insert --system,-- therefore;

Page 2, Column 2, Line 60, Other Publications: Delete "fameless" and insert --frameless-- therefore;

Page 3, Column 1, Line 5, Other Publications: Delete "steroatactic" and insert --stereotactic-- therefore;

Page 3, Column 1, Line 7, Other Publications: Delete "fo" and insert --of-- therefore;

Page 3, Column 1, Line 9, Other Publications: Delete "prosepctive" and insert --prospective-- therefore;

Page 3, Column 1, Line 33, Other Publications: Delete "thhe" and insert --the-- therefore;

Page 3, Column 1, Line 35, Other Publications: Delete "application sof" and insert --application of-- therefore;

Page 3, Column 2, Line 1, Other Publications: Delete "Clincial expereience" and insert --Clinical experience-- therefore; and Signed and Sealed this
Twenty-ninth Day of May, 2018

Andrei Iancu
*Director of the United States Patent and Trademark Office*

CERTIFICATE OF CORRECTION (continued)
U.S. Pat. No. 9,901,375 B2

In the Claims

Column 5, Line 7, Claim 11: Delete "convertion" and insert --convection-- therefore.